United States Patent
Cusimano Reaston et al.

(10) Patent No.: US 8,568,312 B2
(45) Date of Patent: *Oct. 29, 2013

(54) ELECTRO DIAGNOSTIC FUNCTIONAL ASSESSMENT UNIT (EFA-3)

(76) Inventors: MaryRose Cusimano Reaston, Las Vegas, NV (US); Phil Reaston, Las Vegas, NV (US)

(*) Notice: Subject to any disclaimer, the term of this patent is extended or adjusted under 35 U.S.C. 154(b) by 138 days.

This patent is subject to a terminal disclaimer.

(21) Appl. No.: 12/661,240

(22) Filed: Mar. 12, 2010

(65) Prior Publication Data

US 2011/0224503 A1    Sep. 15, 2011

(51) Int. Cl.
A61B 5/00    (2006.01)

(52) U.S. Cl.
USPC ............................ 600/301; 600/300; 128/920

(58) Field of Classification Search
None
See application file for complete search history.

(56) References Cited

U.S. PATENT DOCUMENTS

| | | | |
|---|---|---|---|
| 4,586,515 A | 5/1986 | Berger | |
| 4,667,513 A | 5/1987 | Konno | |
| 4,688,581 A | 8/1987 | Moss | |
| 4,742,832 A | 5/1988 | Kauffmann et al. | |
| 4,800,897 A | 1/1989 | Nilsson | |
| 4,805,636 A | 2/1989 | Barry et al. | |
| 4,834,057 A | 5/1989 | McLeod, Jr. | |
| 4,845,987 A | 7/1989 | Kenneth | |
| 4,886,073 A | 12/1989 | Dillon et al. | |
| 4,928,709 A | 5/1990 | Allison et al. | |
| 4,938,476 A | 7/1990 | Brunelle et al. | |
| 5,012,820 A | 5/1991 | Meyer | |
| 5,038,795 A | 8/1991 | Roush et al. | |
| 5,042,505 A | 8/1991 | Mayer et al. | |
| 5,050,618 A | 9/1991 | Larsen | |
| 5,056,530 A | 10/1991 | Butler et al. | |
| 5,462,065 A | 10/1995 | Cusimano et al. | |
| 5,513,651 A * | 5/1996 | Cusimano et al. | 600/595 |
| 6,678,549 B2 | 1/2004 | Cusimano et al. | |
| 2002/0091308 A1* | 7/2002 | Kipshidze et al. | 600/300 |
| 2002/0198473 A1* | 12/2002 | Kumar et al. | 600/595 |
| 2003/0083720 A1* | 5/2003 | Peterson et al. | 607/88 |
| 2003/0135129 A1* | 7/2003 | Cusimano et al. | 600/546 |
| 2006/0058699 A1* | 3/2006 | Vitiello et al. | 600/546 |
| 2007/0230270 A1 | 10/2007 | Calhoun | |
| 2009/0281448 A1* | 11/2009 | Wright et al. | 600/546 |
| 2009/0326406 A1* | 12/2009 | Tan et al. | 600/546 |

OTHER PUBLICATIONS

Jovanov et al. "A Wireless Body Area Network of Intelligent Motion Sensors for Computer Assisted Physical Rehabilitation" Journal of NeuroEngineering and Rehabilitation 2005, 2:6 doi:10.1186/1743-0003-2-6, Published Mar. 1, 2005.*

* cited by examiner

Primary Examiner — Bill Thomson
Assistant Examiner — Davin K Sands
(74) Attorney, Agent, or Firm — Albert O. Cota

(57) ABSTRACT

An Electro Diagnostic Functional Assessment Unit (EFA-3) that is designed to wirelessly monitor muscle group activity and to provide treatment for humans and animals. The muscle groups include the body, fascial, cervical, thoracic, upper and lower extremities, lumbosacral, bladder, cardiac, and rectal. In large animals the muscle groups include torso, legs, neck and face. The EFA-3 simultaneously correlates the muscle activity EMG with cardiac activity, nerve activity, heart rate, blood flow and brain activity with range-of-motion, grip and pinch assessment and a functional assessment in humans. The EFA-3 is operated by proprietary software (78) which provides testing protocols by utilizing a set of wireless sensor(s) (14-40) that are interchangeable and rechargeable. The treatment includes ultrasound, heat, cold, massage and electrical stimulation.

3 Claims, 4 Drawing Sheets

ELECTRO DIAGNOSTIC FUNCTIONAL ASSESSMENT UNIT (EFA-3)

TECHNICAL FIELD

The invention generally pertains to the field of diagnostic treatment systems, and more particularly to a wireless Electro Diagnostic Functional Assessment Unit (EFA-3) that monitors muscle functions, cardiac functions, nerve functions, nerve conductions, temperature, heart rate, blood flow and brain activity simultaneously with range of motion including lifting, pulling, pushing, gripping and pinching. The EFA-3 also integrates the diagnostic capabilities and delivers site-specific treatment such as ultrasound, heat, cold, massage and electrical stimulation.

BACKGROUND ART

The Occupational Safety and Health Administration (OSHA) has determined that soft tissue injuries are a leading cause of lost work, time and productivity. Soft tissue injuries cost over $200 billion annually in lost man-hours and medical costs. In fact, soft tissue injuries are responsible for 80 percent of all Workers Compensation claims. Soft tissue injuries are often non-specific, difficult to diagnose and treat, and current subjective diagnostics can be a "process of elimination". In addition, it is often difficult to determine when a soft tissue injury has occurred.

In the medical community, it is well known that muscle compensation patterns can be used to differentiate chronic versus acute injuries. Acute injuries are typically exemplified by muscle spasm and hyperactivity. Chronic injuries are typically associated with compensation, bilateral changes, and absence of a reflection relaxation response. It is also a fact that many physicians deal with complaints and injuries that involve soft tissue injury, particularly cervical, thoracic, lumbosacral and extremities. All muscle groups of the body, from the cervical including the mid, thoracic, lumbosacral and upper and lower extremities, can be monitored using the EFA-3 for both humans and animals. This is extremely beneficial because a typical soft tissue injury may be chronic or acute, with no physical indicators. Direct palpation of a soft tissue injury can, in some cases, reveal the nature or type of injury, but this manner of diagnosis relies on static testing and on individual tests that are performed separately, which are less reliable than combining and integrating the evaluations of Electromyography (EMG), range of motion (ROM) and functional assessment. To enhance and correlate the above tests, physiological parameters, cardiac response, temperature, nerve testing, brain wave activity and blood flow can also be monitored.

The combination of these tests, unlike any other test, does not rely on the coefficients of variance but measures muscle activity while simultaneously monitoring range of motion, functional assessment, grip strength, pinch strength, cardiac response, temperature and nerve and brain wave activity either alone or in combination. This dynamic integration provides an analysis of Type I versus Type II motor units, which coordinate with an effort produced by the individual who is being tested. Furthermore, when disc pathology is present there is a chemical released in the individual's blood supply, which causes ischemic changes in the surrounding musculature. The benefit of quantifying these conditions in a non-invasive and portable manner is that the amount of ischemia/vasoconstriction in the surrounding blood tissue correlates with the degree of disc pathology, thereby allowing treatment recommendations to be made, i.e. surgery versus physical therapy. The benefit of the EFA-3 is its ability to monitor and site-specifically treat muscles, nerves and other bodily functions.

In the past, various technological tests such as EMG, range of motion, cardiac information or functional assessments were singularly relied upon to determine the cause of muscle activity. However, when the tests are performed alone they are less objective. By integrating all of the functions of the EFA-3 it is possible to acquire a more objective assessment of any specific treatment.

The costs of treating the above-described problems are expected to increase, especially with OSHA considering new ergonomic standards. With the implementation of the American's with Disabilities Act (ADA) workers compensation claims have increased, especially claims of Carpal Tunnel Syndrome (CTS) which are expected to exceed 40 billion dollars per year within the next five years. CTS problems are also often misdiagnosed, for example, referred pain from the scalene muscle can mimic the symptoms of lunar neuropathy, carpal tunnel syndrome or even thoracic outlet syndrome. The misdiagnosed above problems are in reality a muscle problem in the front of the neck.

A recent study demonstrates that 45 percent of individuals who have undergone CTS surgery receive no relief and show no improvement at a two year follow up. The lack of improvement can be attributed to the inability to identify the soft tissue component. Furthermore, 65 percent of individuals who have undergone back surgery resulted in failed back syndrome or have no relief of symptomology. This can also be attributed to an inability to properly diagnose and age a soft tissue injury. In the past, prior art has not been capable of performing a proper diagnosis.

Until the advent of the EFA-3 it was not possible to incorporate all of functions required to perform a comprehensive diagnostic test in a reliable, cost effective and user-friendly manner. The uniqueness of the EFA-3 is the utilization of remote and wireless sensor(s) which provide portability and increased ease of use. The wireless sensor(s) can have a disposable component, and any proprietary sensor(s) that are not disposable have their own battery-recharging unit. This allows for no down-time during monitoring and, since the sensor(s) can be interchangeable, if one sensor(s) is not functioning, a replacement is immediately available. Therefore, an unlimited combination of testing possibilities is available depending on the protocols required. The EFA-3 is operated remotely, by utilizing GiFi, WiFi, ZIGBEE™, BLUETOOTH™, or any other standard or proprietary wireless system.

A search of the prior art did not disclose any patents that read directly on the claims of this instant invention, however the following patents and publications are considered related:

| Pat. No. | INVENTOR | ISSUE DATE |
|---|---|---|
| 6,678,549 | Cusimano, et al | 13 Jan. 2004 |
| 5,513,651 | Cusimano, et al | 7 May 1996 |
| 5,462,065 | Cusimano, et al | 31 Oct. 1995 |
| 5,042,505 | Mayer, et al | 27 Aug. 1991 |
| 4,688,581 | Moss | 25 Aug. 1987 |
| 4,667,513 | Konno | 26 May 1987 |
| 20060058699 | Vitiello et al | 19 Apr. 2005 |

The U.S. Pat. No. 6,678,549, which is owned by the applicants of the instant application, discloses a system that combines Electromyography (EMG), Range of Motion (ROM), and Nerve Conduction Velocity (NCV). It differs from the instant application in that it is not an integrated unit and is only used to test humans. The system also does not allow for remote monitoring, blood flow monitoring or the use of various Range of Motion (ROM) implements, and uses an interface that does not allow for the rapid exchange of data.

The U.S. Pat. Nos. 5,513,651 and 5,462,065, which are owned by the applicants of the instant application, disclose an integrated movement analyzing system (IMA) that utilizes surface EMG in combination with range of motion and functional capacity testing to monitor muscle groups in the human body. The system consists of an integrated movement analyzer (IMA) that receives inputs from surface EMG electrodes, a range of motion analyzer (ROMA), and a functional capacity sensor(s). When performing upper and lower back testing, the ROMA is connected between the subject's upper back and the lower back by a shoulder harness and a waist belt.

For cervical testing, the ROMA is connected between the subject's head and the upper back by a cervical cap and the shoulder harness. The output of the IMA is provided via an analog to digital converter to a computer. The computer, in combination with a software program, produces an output consisting of comparative analytical data. This data is taken via a parallel port and multiple a/d cards while the subject is not isolated. This system can not be used remotely, has hardwired cables and does not have the capability to monitor physiological properties except for EMG, range of motion, FCE, pinch and grip.

The U.S. Pat. No. 5,042,505 discloses an electronic device for measuring relative angular positional displacement and angular range of motion for body segments and articulating joints of the human skeleton. The device has a hand-held interface unit, which is placed against the body segment or joint to be tested. Mounted within the housing of the interface unit is a shaft with a pendulum at one end and an optical encoder at the other. As the body segment rotates or the joint articulates, the pendulum swings in the direction of gravity, causing the shaft to rotate. The optical encoder generates an electrical signal representative of the amount of rotation of the shaft. The generated signal is fed to a microscope which processes the signal and produces on a display the change in angular position relative to the initial angular position or the angular range of motion of the body segment or articulating joint.

The U.S. Pat. No. 4,688,581 discloses an apparatus and a method for non-invasive in-vivo determination of muscle fiber composition. The method includes the steps of electrically stimulating a chosen muscle, determining the stimulation current, measuring the electrical stimulating a chosen muscle, determining the stimulation current, measuring the electrical potential of the muscle, the contraction time and the force produced by the contraction. By intercorrelating the data by multiple regression, the type, percentage and size of the muscle fibers within the muscle stimulated can be determined. The apparatus determines muscle composition and includes a muscle stimulator of controlled voltage, electromygram equipment and a force transducer, that in combination provide a tension curve as well as force measurements.

The U.S. Pat. No. 4,667,513 discloses an apparatus and a method for estimating the degree of the fatigue and pain of muscles. The apparatus tests subjects of different weights on the same basis by deriving the variation in the muscular strength such as dorsal muscular strength, shoulder muscular strength, grasping strength and the like. An analogous electric signal integrates the muscular output and provides an integrated value of the electromyogrammatic amplitude by processing the voltage induced from the muscle to be tested through an electromygram amplitude and waveform processor. The ratio between these integrated values after correlating the ratio with the weight/muscular strength coefficient is digitally displayed.

The 20060058699 publication discloses a non-integrated system that is used to test humans by combining EMG and ROM. The system does not allow remote monitoring, blood flow monitoring or different ROM, utilizes an interface that does not allow for the rapid exchange of data and uses multiple data acquisition cards. The system also uses an electromagnetic field for range of motion that can be ineffective and even harmful to individuals who have post surgical hardware or pacemakers.

For background purposes and as indicative of the art to which the invention relates, reference may be made to the following remaining patents and publications found in the search:

| Pat. No. | INVENTOR | ISSUE DATE |
|---|---|---|
| 5,056,530 | Butler, et al | 15 Oct. 1991 |
| 5,050,618 | Larsen | 24 Sep. 1991 |
| 5,042,505 | Meyer, et al | 27 Aug. 1991 |
| 5,038,795 | Roush, et al | 13 Aug. 1991 |
| 5,012,820 | Meyer | 7 May 1991 |
| 4,938,476 | Bryunnell, et al | 3 Jul. 1990 |
| 4,928,709 | Allison, et al | 29 May 1990 |
| 4,886,073 | Dillion, et al | 12 Dec. 1989 |
| 4,845,987 | Kenneth | 11 Jul. 1989 |
| 4,834,057 | McLeod, Jr | 30 May 1989 |
| 4,805,636 | Barry, et al | 21 Feb. 1989 |
| 4,800,897 | Nilsson | 31 Jan. 1989 |
| 4,742,832 | Kauffmann, et al | 10 May 1988 |
| 4,667,513 | Konno | 26 May 1987 |
| 4,586,515 | Berger | 6 May 1986 |
| 20070230270 | Calhoun; Robert B. | 4 Oct. 2007 |

DISCLOSURE OF THE INVENTION

The Electro Diagnostic Functional Assessment Unit (EFA-3) is designed to integrate physiological monitoring and functional assessment, i.e. muscles, nerves, brain waves, cardiac, blood flow, heart rate, range of motion, temperature and functional abilities into a single integrated test unit. The EFA-3 is operated by proprietary software which utilizes wireless sensor(s) that are interchangeable, rechargeable and that can process data without the need for a computer and/or smartphone. The EFA-3 is also capable of delivering site-specific treatment as directed by the unit's diagnostic testing measures.

In its basic design configuration, the EFA-3 is comprised of the following elements:

A. A data transmitting unit comprising:
  (1) At least one wireless sensor(s) having an input and an output, wherein the input is attached to a selected area of a human or an animal subject,
  (2) A wireless processing circuit having means for receiving and processing the output from the at least one sensor(s) and producing an output,
B. A receiving and transmitting interface having means for receiving the output from the wireless processing circuit and producing an output that is applied into space,
C. A data receiving unit having means for receiving and processing the output from the receiving and transmitting interface and producing an output that is indicative of the subject's test results, and D. a receiving and transmitting interface having means for delivering site-specific treatment modalities such as electrical stimulation, ultrasound, heat, cold or other therapeutic modalities that are determined by EFA-3's diagnostic capabilities.

The above elements function in combination to provide an EFA-3 that:

identifies compliant individuals, malingering individuals, and individuals who have pain that cannot produce a large output, diagnoses actual injuries, cardiac problems, fecal or urinary incontinence, brain functions, nerve entrapments and allows the acquired data to be analyzed to determine and deliver appropriate treatment, determines the extent of myofascial injuries and if the injuries relate to any mechanics of an injury or pathology, determines appropriate treatment for myofascial injuries, assesses the extent of nerve injuries and determines if the injury relates to any other injury or pathology, assesses the extent of a fecal or urinary incontinence problem and determines if the problem relates to any other injury or pathology, assesses the heart rate and determines if the heat rate relates to compliance, injury or pathology, allows for cardiac and myofascial monitoring to determine cause of pathology and outlines treatment, assesses brain activity that relates to an injury or pathology, allows muscle pathology to be assessed above and below the area of a reported injury, which allows for the extent of the injury to be established to determine proper treatment, allows for temperature and nerve conduction velocity to be measured to ascertain not only myofascial, nerve and structural injuries but also the possibility of permanent disability, surgical intervention, treatment and vocational rehabilitation in both humans and large animals, provides real-time diagnosis of muscle activity, EKG activity, skeleton activity, nerve activity, bladder activity, rectal activity, brain activity and temperature, provides a tool for establishing an evaluation and treatment program, provides site-specific treatment, provides remote monitoring to allow experts who are not at a subject's physical location to evaluate the subject, assesses chronic versus acute injuries by evaluating muscle composition, evaluates EKG activity as a preventative measure to prevent cardiac problems, evaluates brain activity as a preventative measure, evaluates bladder activity as a preventative measure, evaluates rectal activity as a preventative measure, assesses nerve conduction velocity with temperature electrodes for injury as well as prevention assessments, assists physicians who care for athletes and determines the extent of sports-related muscular skeletal injuries, and can provide accurate data that is used for designing site-specific treatment protocols or training regimens.

can be used as a pre-physical examination to allow trainers of both humans and animals to address otherwise undiagnosed deficiencies in the muscular, skeletal, cardiac, nerve, blood flow and temperature, and assesses the clinical significance of disc pathology.

In summary, the EFA-3 identifies the severity of injuries and allows for future diagnostic and treatment programs to be established and delivered. The diagnostic and treatment programs consider both the needs of the treated person or animal, and the need to contain runaway costs of potential long-term or unsubstantiated cases.

In view of the above disclosure, the primary object of the invention is to provide an EFA-3 that monitors muscle activity in humans and animals which includes any muscle group in the fascial, cervical, thoracic, upper and lower extremities, lumbosacral, bladder, cardiac, and rectum. The EFA-3 simultaneously correlates the muscle activity EMG with cardiac activity, nerve activity, heart rate, blood flow and brain activity with range-of-motion (ROM), grip and pinch assessment and a functional assessment in humans. Temperature and nerve conduction velocity (NCV) can also be monitored in humans and animals. The EFA-3 also can deliver site-specific treatment based on the diagnostic evaluations.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms that disclose a preferred embodiment of a third generation Electro Diagnostic Functional Assessment Unit (hereinafter "EFA-3"). The EFA-3 is comprised of a portable, self-contained and non-loading unit that is designed to test humans and animals and deliver treatment. The testing is performed by monitoring muscle functions, cardiac functions, nerve functions, nerve conduction velocity, temperature, heart rate, blood flow and brain activity simultaneously with range of motion tests that include lifting, pulling, pushing, gripping and pinching. In addition the EFA-3 comprises wireless sensor(s) that deliver site-specific treatment which is performed from information that is derived from the combined use of multiple sensors.

Figure 1A:
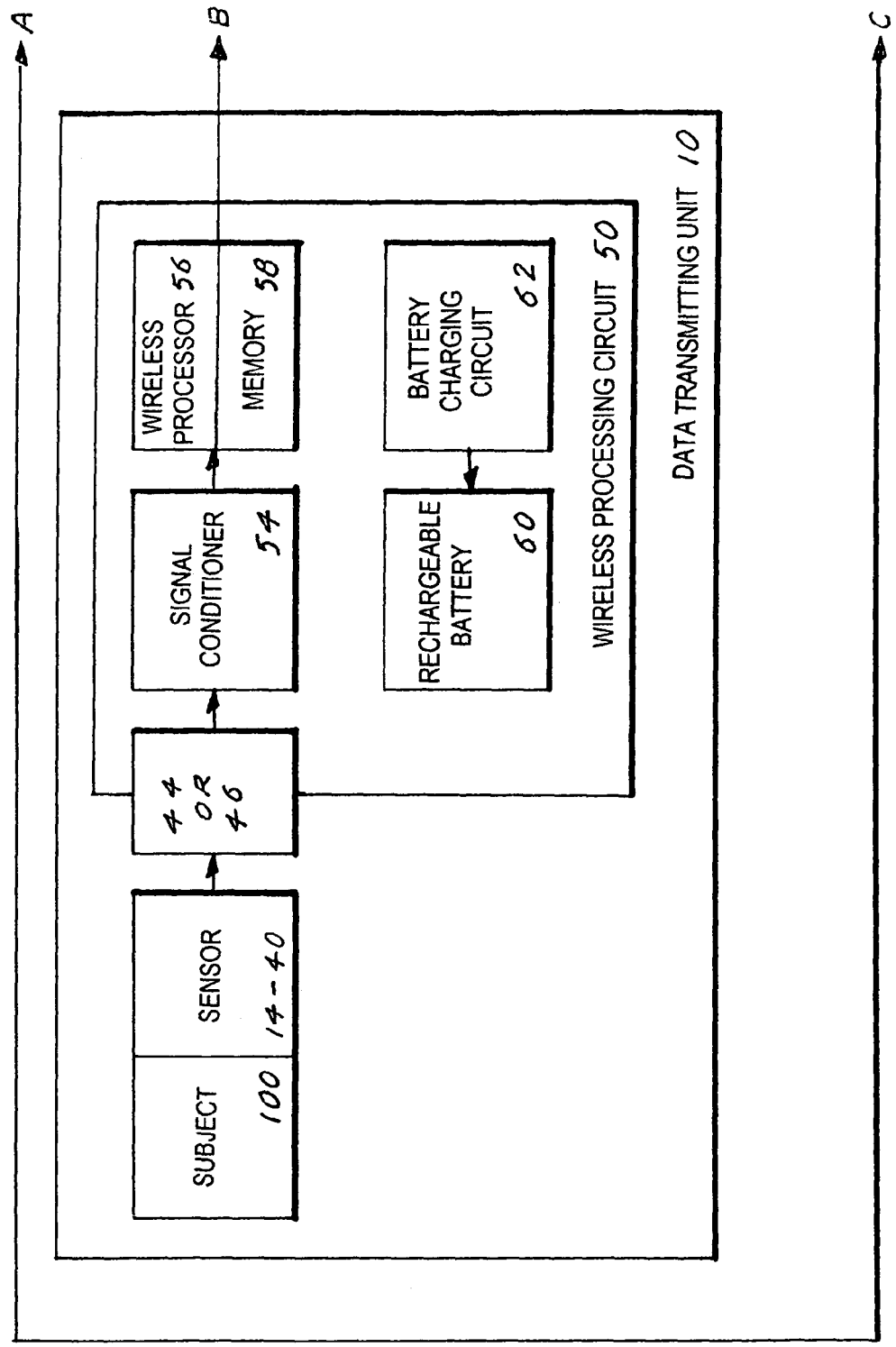
FIG. 1A is a block diagram of the EFA-3 showing the basic elements that comprise the data transmitting unit which includes the sensor(s) and the wireless processing circuit.
Figure 1B:
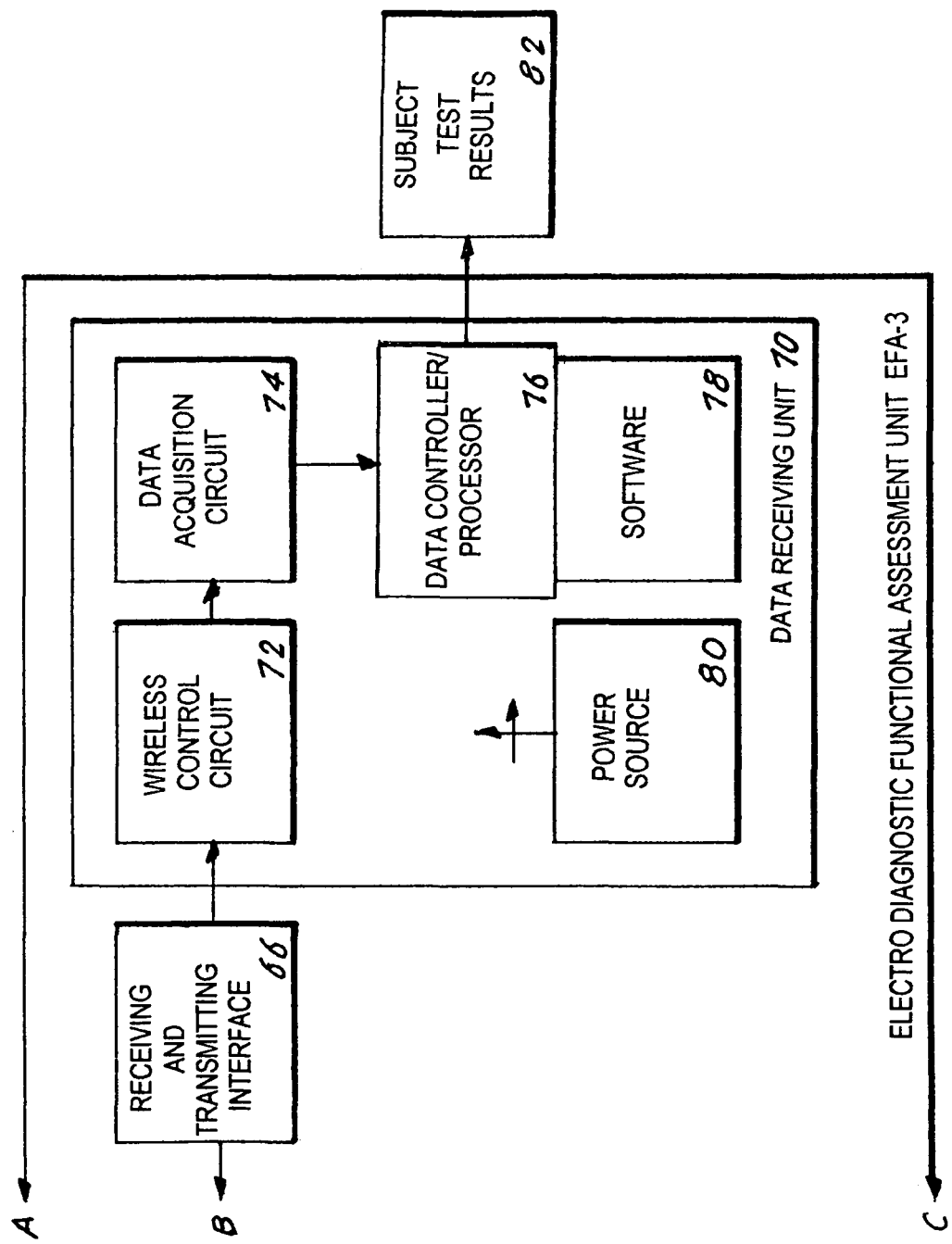
FIG. 1B is a continuation block diagram of the remaining elements that comprise the EFA-3, namely the receiving and transmitting interface, the data receiving unit and the subject's test results.

The preferred embodiment of the EFA-3, as shown in FIGS. 1A, 1B, 2 and 3, is comprised of three major elements: a data transmitting unit 10, as shown in FIG. 1A, which is further comprised of a plurality of sensor(s) 14-40 and a wireless processing circuit 50; and as shown in FIG. 1B, a receiving and transmitting interface 66; and a data receiving unit 70. A wireless unit to deliver treatment modalities.

Figure 2:
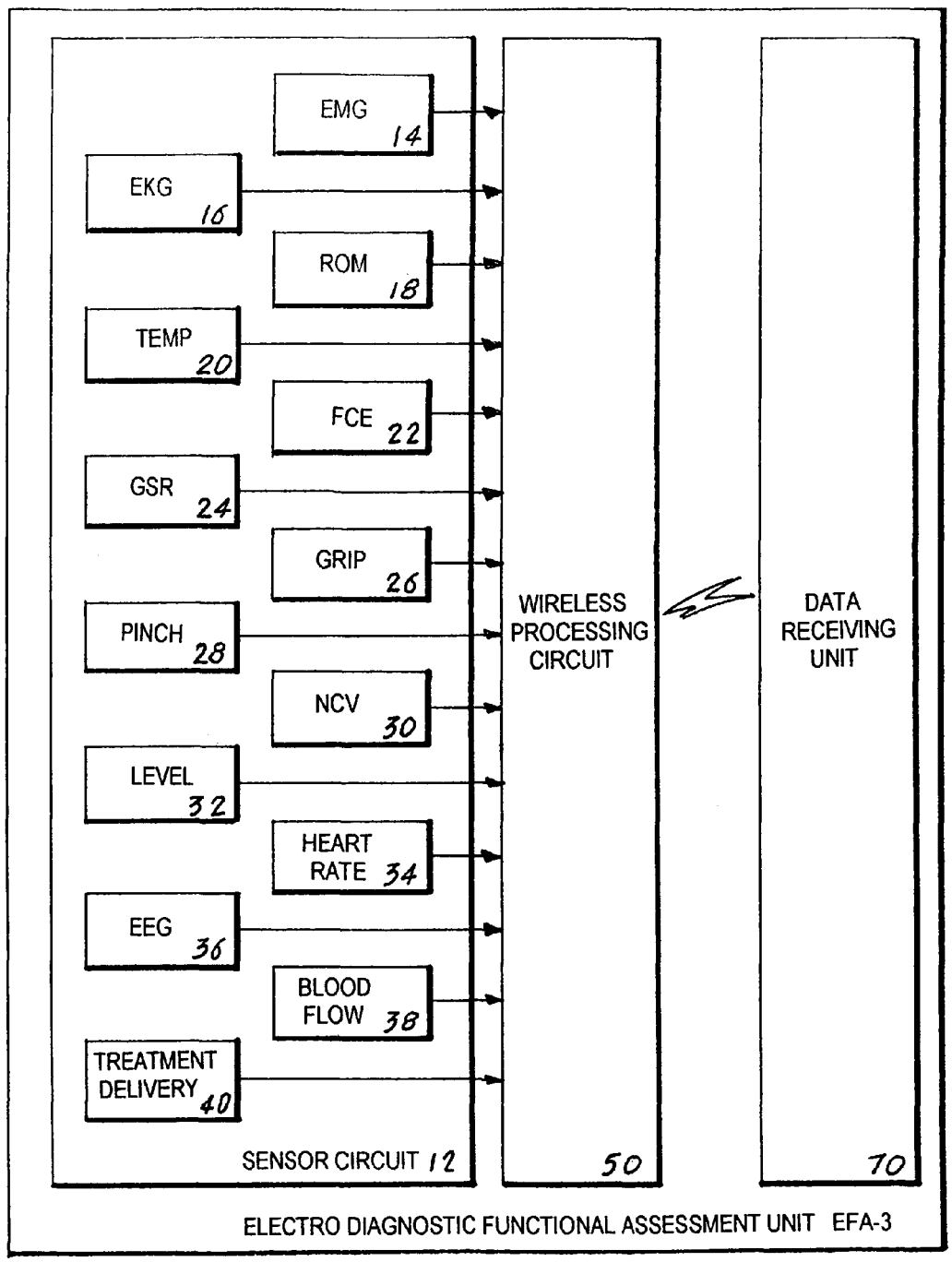
FIG. 2 is a block diagram showing a plurality of wireless sensor(s) that are each connected to a corresponding plurality of wireless processing circuits which are connected to a data receiving unit. For simplicity, the plurality of wireless processing circuits are shown as a single block.
Figure 3:
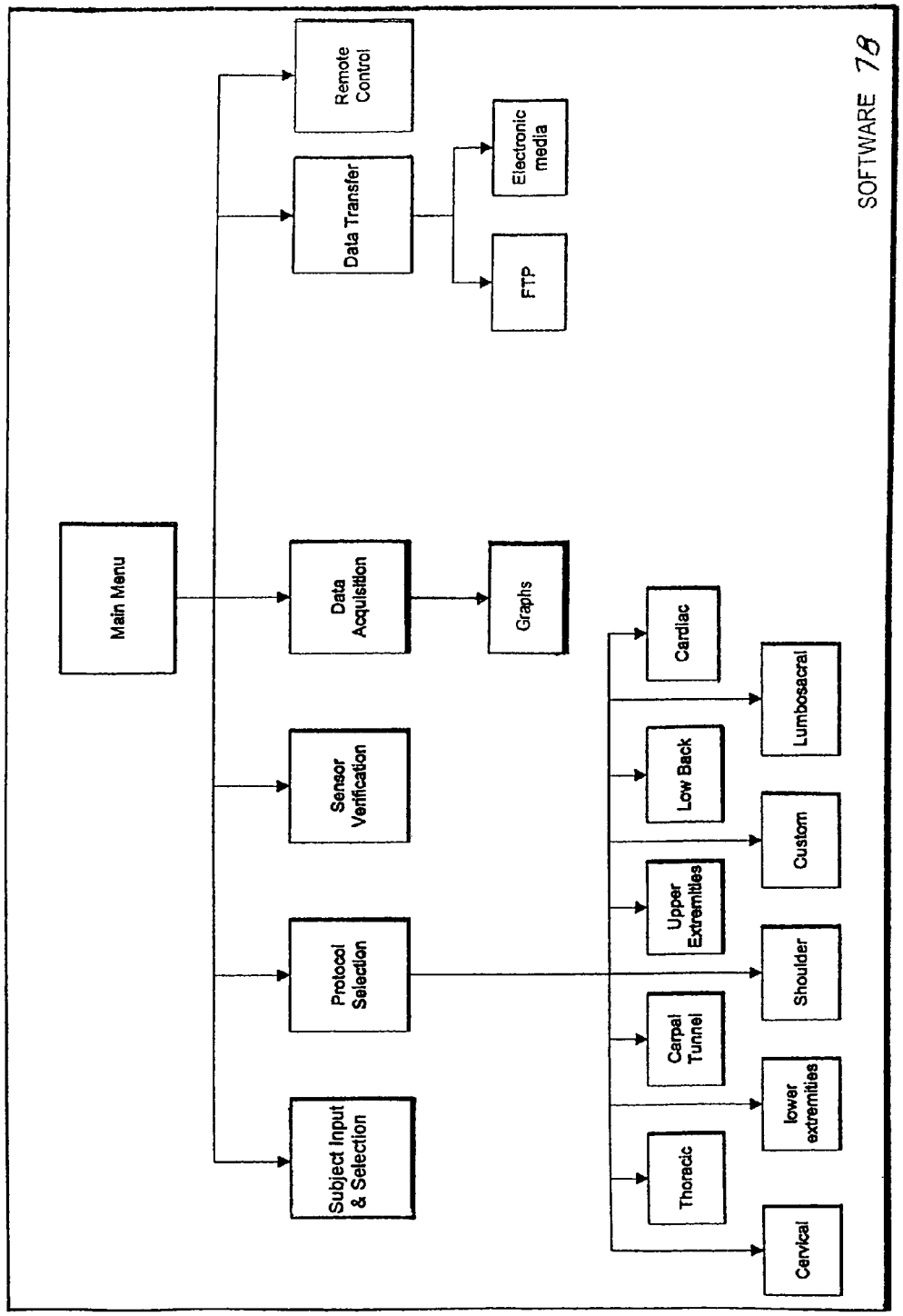
FIG. 3 is a module flow-down diagram of the EFA-3 software program.

The sensor(s), as shown in FIG. 2, are preferably comprised of the following wireless sensor(s):

At least one EMG sensor 14,
At least one EKG sensor 16,
At least one range-of-motion (ROM) sensor 18, At least one temperature sensor 20, At least one functional capacity evaluation (FCE) sensor 22, At least one Galvanic Skin Response (GSR) sensor 24.

At least one grip sensor 26.

At least one pinch sensor 28,

At least one nerve conduction velocity (NCV) sensor 30,

At least one level sensor 32,

At least one heart rate sensor 34,

At least one EEG sensor 36,

At least one blood flow sensor 38, and

At least one treatment delivery mechanism 40.

The ROM sensor(s) 18 is utilized for measuring the range of motion of the cervical, thoracic, lumbosacral, upper extremity, lower extremity and digits. The ROM measures a person's lateral movement, flexion, extension, rotation, abduction, adduction, lateral movements and internal and external rotation, with each having a minimum of six degrees of freedom. The ROM incorporates either accelerator, potentiometer or gyroscope systems where each system includes three precision potentiometers, hermetically sealed accelerometers or gyroscopes. The ROM sensor(s) is a wireless sensor(s) integrated into the system.

The functional capacity evaluation (FCE) sensor(s) 22 measures a person's lifting, pulling and pushing capability and functions by utilizing load cells having a range from 0 to 300 pounds. The grip sensor(s) 26 measures a person's hand grip strength which is measured by a load cell that produces an output that is proportional to the hand grip force. The pinch sensor(s) 28 utilizes a load cell having a range from 0 to 50 pounds. The cell is placed between a person's thumb and index finger and is squeezed to produce an output. The temperature sensor(s) 20 measures a person's temperature in Centigrade and Fahrenheit. The NCV sensor(s) 30 measures nerve conduction velocity in any muscle group in a person's body. The measurement is made with preset electrodes that monitor the temperature and produce an output that is proportional to the nerve conduction. The EKG sensor(s) 16 measures a person's cardiac response at a frequency between 3 to 10 hertz. The EEG sensor(s) 36 measures a person's brain activity. The heart flow sensor(s) 34 measures a person's heart rate, and the blood flow sensor(s) 38 measures a person's blood flow. The EMG sensor(s) 14, when performing NCV, includes a separation bar which can be locked at a distance between 3 to 5 inches. The separation bar allows two active electrodes to remain isolated from each other. Additionally, the EMG protocol can also include a temperature sensor(s) that allows temperature readings to be taken in combination with other EMG/NCV sensor(s) readings. The EFA-3 also incorporates a treatment delivery sensor(s) 40 which is wireless and can deliver such treatment modalities as heat, cold, ultrasound and electrical stimulation.

Each of the wireless sensor(s) 14-40 has an input and an output. The input is attached to a selected area of a subject 100 undergoing a testing protocol. The subject 100 can consist of either a human or an animal. The wireless processing circuit 50, as shown in FIG. 1A, is further comprised of a signal conditioner 54, a wireless processor(s) 56/memory 58, a rechargeable battery 60 and a battery charging circuit 62.

The sensor(s) each includes an input and an output, wherein the input is connected to a subject and the output is sent to a control device. The sensor(s) circuit 12 which includes sensor(s) 14-40, as shown in FIG. 1A and FIG. 2, can be either hardwired 44 to the signal conditioner 54 or a connector-pair 46 can be utilized.

The signal conditioner 54 has means for receiving and optionally filtering and amplifying the output from the sensor(s) 14-40 and for producing an output. The output from the signal conditioner 54 is applied to the wireless processor 56 which consists of a microcontroller. The wireless processor 56/memory 58 has means for processing the signal applied from the signal conditioner 54 and to produce an output that is applied to the input of the receiving and transmitting interface 66. The interface 66, as shown in FIG. 1B, utilizes a wireless system that is selected from the group consisting of GiFi, WiFi, ZIGBEE™ and BLUETOOTH™ or any other proprietary or non-proprietary wireless system.

The elements that comprise the data transmitting unit 10 are powered by a battery that preferably is comprised of the rechargeable battery 60 which is selected to provide the required voltage/current and that can be recharged by means of the battery charging circuit 62, as shown in FIG. 1A. Additionally, the elements that comprise the data transmitting unit 10, namely the sensor(s) 14-40, the signal conditioner 54, the processor 56/memory 58 and the rechargeable battery 60 can be integrated into a single unit (not shown).

The output from the receiving and transmitting interface 66 is applied to a wireless control circuit 72 which controls the receiving and transmitting of the wireless signal. The wireless control circuit 72 is an element of the data receiving unit 70, as shown in FIG. 1B, which is further comprised of a data acquisition circuit 74, a data controller/processor 76 that is operated by software 78, and a power source 80. The data controller/processor 76 can be comprised of a computer having wireless capability and or a smartphone. The power source 80 can be comprised of either a battery or a utility power source that can range between 120 to 250 volts a-c at a frequency between 50 to 60 hertz. The utility power source includes means for converting the a-c voltage to a regulated d-c voltage.

The data acquisition circuit 74 functions in combination with the receiving and transmitting interface 66 to buffer and separate the data applied by each of the sensor(s) into discreet signals that are then applied to the data controller/processor 76. The data acquisition circuit 74 can be eliminated from the data receiving unit 70 if the wireless control circuit 72 has sufficient power and means for producing an output that can be applied directly to the data controller/processor 76.

The treatment circuit functions in combination with the data acquisition circuit 74 to deliver site-specific treatment as required such as ultrasound, heat, cold and electrical stimulation. The data controller/processor 76, in combination with the software 78, produces an output that is indicative of a subject's test results 82, as shown in FIG. 1B.

The software 78 that operates the data controller/processor 76 is comprised of the following modules that flow-down from a main menu:

a) subject input and selection, b) protocol selection further comprising:
  (1) cervical,
  (2) thoracic,
  (3) lower extremities,
  (4) carpal tunnel,
  (5) shoulder,
  (6) upper extremities,
  (7) custom,
  (8) lower back,
  (9) lumbosacral, and
  (10) cardiac, c) sensor(s) verification, treatment verification and delivery, d) data acquisition further comprising graphs, e) data transfer further comprising:
   (1) file transfer protocol (FTP) and
   (2) electronic media, and
f) remote control.

The major modules that comprise the EFA-3 software 78 are described below:

Main menu—provides start up routines and initialization routines for the EFA-3. Upon startup, a main menu window is displayed and user commands are available. To enforce correct sequencing of the software some commands are not available until prerequisite steps have been performed.

Subject Input and selection—provides services to add/edit a new subject, select previous subjects for retest and select a subject for demonstration. Provides interactive forms for the collection of subject data. After all data is validated, control is returned to the subject input and selection module, which then returns control to the Main menu.

Protocol Selection—provides for selection of the protocol (sequence of steps) for the current test. The software has available several pre-defined protocols and custom protocols can be added as needed. Each protocol gives the operator instructions as to what the subject should do and instructions on the placement of the sensor(s). This module also provides support for muscle group range of motion, nerve conduction velocity, temperature, cardiac, and treatment.

Sensor(s) Verification—provides testing of the sensor(s) to view accuracy of placement, data and activity.

Data Acquisition—provides data capture routines. Data is collected and monitored via the EFA-3. If a lead fail is detected during a data capture, the Data Acquisition circuit 74 cancels the data capture and sends a warning to the operator. A successful data capture results in a data file being saved to an internal hard drive. If the test is being performed in real-time the results are displayed immediately. In addition, the data acquisition circuit 74 provides treatment recommendations that are delivered via the treatment sensor(s) 40.

Data Transfer—provides routines to transfer data to a central site for processing. The transfer can be over an Internet connection (either dial up or networked), by electronic media or through a delivery service (USPS, UPS, etc).

Remote Control—provides for testing to be conducted from a remote location.

The EFA-3 combines a load cell and two strain gauges to determine a subject's lifting, pushing, pulling, gripping and pinching capabilities in combination with range of motion. The EFA-3 can also function in combination with peripheral devices that provide the monitoring of range of motion, blood flow, temperature, lifting, gripping, pinching temperature and brain waves. The wireless sensor(s) 14-40 are designed to process information utilizing the proprietary software 78. To input data a keyboard or a telephone can be used. The data is wirelessly transferred from the sensor(s) circuit 12 to the data receiving unit 70 via a standard or a proprietary wireless protocol.

During an injury to a muscle and/or a fascial element, many pathophysiological processes occur which follow a predictable pattern. When a muscle is strained, the fibers of the muscle are damaged and cells within the muscles are ruptured. The ruptured cells release substances which cause the muscle to reflexively tighten. Muscles that cause an action (agonist) and muscles which prevent the action (antagonist) are monitored. Muscle groups which are distant from the injury site may not be performing properly function as they are compensating for the loss of function due to the injury. Site-specific treatment can be delivered to address such issues. The greater the pattern of compensation the more longstanding the injury.

The absence of the flexion relaxation response of the cervical, thoracic and lumbosacral spines are also consistent with a chronic injury. The EFA-3 monitors muscle activity amplitude changes that correlate with contracture and frequency changes which pertain to spasms. Ischemic changes are monitored and bilateral assessments are made for comparison. Muscle groups above and below the injury site are also monitored to determine primary, secondary and tertiary patterns.

The EFA-3 can also age an injury which is multi-factorial and involves not only the testing of muscle groups but their inter-relationship with each other, in combination with range of motion (ROM) testing. The ROM testing is performed with either the use of potentiometers, inclinometers or accelerometers into an upper, middle and lower section to correlate with spinal conditions such as straightening of the cervical spine, spondolyothesis, degenerative disk disease and post-surgical changes. The ROM testing can also measure the motion of other parts of the body such as the wrist, hand, arm or foot.

The muscle groups monitored by the EFA-3 are: fascial, cervical, thoracic, lumbosacral, upper extremity and lower extremity, cardiac, bladder and rectal in both humans and animals. Data pertaining to each muscle group is typically taken in the following steps, while the monitored muscle activity or group is:

At rest,
Going through a range of motion protocol,
Return to rest,
Being applied with a functional assessment, in the human's case: gripping, pinching, lifting, pulling, pushing, and other assessment for that muscle group.
Return to rest, The following data can also be monitored if required for a particular test:

ECG activity,
temperature,
EEG activity,
heart rate,
blood flow,
EEG activity,
bladder function,
rectal function, and
position of the body.

The above tests also allow the EFA-3 to determine muscle tone (contracture amplitude), muscle spasms (frequency), blood flow to muscles (vasoconstrictive states), muscle activity (frequency and recruitment patterns), muscle response (fatigue), cardiac response (EKG), nerve responses, heart rate, blood flow, brain activity (EEG), positional functions and temperature in both humans and animals. Thus the EFA-3 can assess the condition and the dynamic functions of any particular muscle or muscle group in the body for animals and humans. The EFA-3 can perform tests in any combination via the wireless sensor(s) circuit 12 and the data can be transmitted via a standard or proprietary wireless protocol. Site-specific treatment can then be delivered.

The EFA-3 sensor(s) have means for processing the signals, which operate the sensor(s) and are integrated as directed by the software. The EFA-3 sensor(s), which are shown in their overall relationship with the EFA-3 in FIG. 2, conduct the signal processing at the site to avoid cumbersome cables, provide more accurate readings and deliver treatment.

Since the sensor(s) are wireless there is no need to isolate the subject from potentially dangerous voltages. The wireless sensor(s) are connected to the subject with either pregelled silver chloride electrodes for EEG, EMG or EKG or via an adhesive or tape for all other sensor(s) or with treatment via sensor(s) that can deliver, stimulation, heat, cold, massage or ultrasound.

A lead failure, which is controlled by the data acquisition routine of the software 78, has means for determining if the EMG/EKG/NCV/EEG sensor(s) leads are properly attached by measuring the impedance of the muscle and the surrounding skin area. The leads-off detection is processed at the test site and has means for producing a display when an electrode is not properly attached to a muscle or the surrounding skin or there is excessive activity coming from the test site. This determination is made by measuring the impedance of each electrode.

Operation:

To conduct a test, a subject's muscle activity, cardiac activity, range-of-motion, functional activity, nerve conduction velocity studies, brain activity and temperature are analyzed. The analysis is performed by attaching wireless sensor(s) to selected muscle groups, nerve groups, brain and/or cardiac groups on the subject and measuring their electrical activity. The muscle groups in the measurement process are as follows:

Measure fascial muscle groups by placing a range-of-motion sensor(s) on the subject's head and an EMG sensor(s) on the subject's facial muscles and take measurements while the subject is:
At rest,
Performing the selected range-of-motion and functional protocols, and
Returned to rest,
measure the cervical muscle groups by placing a range-of-motion sensor(s) on the subject's head and take measurements while the subject is:
At rest,
Performing the selected range-of-motion and functional protocols, and
Returned to rest,
measure the thoracic muscle group by placing the ROM sensor(s) at the center of the subject's torso and shoulders and take measurements while the subject is:
At rest,
Performing the selected range-of-motion and functional protocols, and
Returned to rest,
measure the chest muscle groups by placing the ROM and EMG sensor(s) on the muscles and the ROM sensor(s) on the subject's torso and shoulders/midback and take measurements while the subject is:
At rest,
Performing the selected range-of-motion and functional protocols, and
Returned to rest,
Measure the lumbosacral muscle group by placing the EMG and ROM sensor(s) at the center of the subject's lower spine and take measurements while the subject is:
At rest,
Performing the selected range-of-motion and functional protocols, and
Returned to rest,
measure the lower and upper extremities by placing EMG sensor(s) on the front and back of the subject's upper and lower extremities and also placing a ROM sensor(s) on the extremities and take measurements while the subject is:
At rest,
Performing the selected range-of-motion and functional protocols and assessments, and
Returned to rest,
Measure the foot muscles of a subject by placing the EMG sensor(s) on and the ROM sensor(s) in the correct place and take measurements while the subject is:
At rest,
Performing the selected range-of-motion and functional protocols, and
Returned to rest,
for the upper extremities in a human's muscle groups the EMG and ROM sensor(s) are monitored in addition to the rest step and performing range of motion testing. The subject is also tested for grip and pinch strength before returning to rest. These muscle readings are also true for muscles or upper and lower extremities. In addition, cardiac output can be monitored with EKG and range of motion while the subject is:
At rest,
Performing the selected range-of-motion and functional protocols, and
Returned to rest,
Nerve conduction velocities are also monitored while the subject's temperature is monitored and can include range of motion measurements.
Monitor the blood flow and heart rate,
Monitor the brain activity, and
Monitor the bladder and rectal functions,
The muscle groups are classified as follows:
The fascial muscles,
The cervical muscles in humans with the following same analogy for animals, the cervical muscles comprise the muscles in the anterior and posterior cervical musculature and lateral musculature, including but not limited to, sternocleidomastoid, scalene paracervical and upper trapezii,
The thoracic muscle groups in humans, with the same analogy in animals, include, but are not limited to: mid trapezii, lower trapezii, paraspinal muscles T5-T8, T8-T12, teres, serratus, and latissimus dorsi,
The chest musculature includes the pectorals muscles, the abdominal muscles and the same analogy in animals,
The lumbosacral muscle group includes the paraspinal muscles L1-S1 quadratus, lumborum, gluteal musculature, abdominal and hamstrings with the same corresponding musculature in animals,
The lower extremity muscle groups include the muscles in the pelvis, legs and feet, and with the same analogy in animals,
The foot muscle group includes the muscles in the feet with the same analogy in animals.
The upper extremity groups include the deltoid, biceps, triceps, wrist flexors and extensors, and thenar muscles,
The hand muscle group,
The rectal muscles, and
The bladder muscles.

Once issues are identified the treatment sensor(s) 40 may deliver the site-specific treatment.

While the invention has been described in detail and pictorially shown in the accompanying drawings it is not to be limited to such detail, because many changes and modifications may be made to the invention without departing from the spirit and the scope thereof. Hence, it is described to cover any and all modifications and forms, which may come within the language and of the scope of the claims.

The invention claimed is:

1. An electro diagnostic functional assessment unit (EFA-3) comprising:
   a) a data transmitting unit comprising a plurality of wireless sensors, that monitor EMG, EKG, nerve conduction velocity (NCV) with rang of motion (ROM), functional capacity evaluation (FCE), and pinch or grip, wherein said sensors function together to derive specific data, wherein each sensor has an input and an output, wherein the input is attached to a selected area of a subject that is undergoing a testing protocol, wherein said sensors provide the data pertaining to the EMG, EKG, NCV with ROM, FCE, and pinch or grip, wherein the acquired data in combination are used to provide site-specific treatment with said EFA-3, b) a receiving and transmitting interface that utilizes a wireless system having means for receiving the output from said wireless sensors for the EMG, EKG, FCE, NCV with ROM, and pinch or grip and producing an output that is applied to said sensors for providing site-specific treatment, and c) a data receiving unit comprising =a treatment delivery mechanism for delivering site-specific treatment that is selected from the group consisting of ultrasound, electrical stimulation, heat, cold, and massage that is performed from the information derived from the combined use of the EMG, EKG, NCV with ROM, FCE, and pinch or grip.

2. The EFA-3 as specified in claim 1 wherein said plurality of wireless sensors comprise:
   a) at least one EMG sensor,
   b) at least one EKG sensor,
   c) at least one rang-of-motion (ROM) sensor,
   d) at least one functional capacity evaluation (FCE) sensor,
   e) at least one grip sensor,
   f) at least one pinch sensor, and
   g) at least one treatment delivery mechanism.

3. An electro diagnostic functional assessment unit (EFA-3) comprising:
   a) a plurality of wireless sensors, wherein said sensors each have an input and an output, wherein the input is attached to a selected area of a subject that is undergoing a testing protocol, wherein said sensors provide data pertaining to EMG, EKG, nerve conduction velocity (NCV) with range of motion (ROM), functional capacity evaluation (FCE), and pinch or grip, which are used in combination to provide site-specific treatment with said EFA-3,
   b) a data acquisition circuit having means for receiving and processing the output from said plurality of wireless sensors and producing an output that delivers site-specific treatment based on the data derived in combination from the EMG, EKG, nerve conduction velocity (NCV) with range of motion (ROM), functional capacity evaluation (FCE), and pinch or grip, and
   c) a treatment delivery mechanism for delivering a site-specific treatment that is selected from the group consisting of ultrasound, electrical stimulation, heat, cold, and message used with said EFA-3.

* * * * *